United States Patent [19]

Bradshaw

[11] Patent Number: 4,967,766
[45] Date of Patent: Nov. 6, 1990

[54] IMPLANTABLE ENDOCARDIAL LEAD WITH FIXATION APPARATUS RETRACTALBE BY A LANYARD

[75] Inventor: James I. Bradshaw, Surfside, Tex.

[73] Assignee: Intermedics, Inc., Angleton, Tex.

[21] Appl. No.: 352,739

[22] Filed: May 16, 1989

[51] Int. Cl.$^5$ .............................................. A61N 1/05
[52] U.S. Cl. .................................. 128/785; 128/642
[58] Field of Search ............... 128/639, 642, 783, 784, 128/785, 786, 790, 419 P

[56] References Cited

U.S. PATENT DOCUMENTS

| 3,974,834 | 8/1976 | Kane | 128/785 |
|---|---|---|---|
| 4,146,036 | 3/1979 | Dutcher et al. | 128/785 |
| 4,217,913 | 8/1980 | Dutcher | 128/785 |
| 4,381,013 | 4/1983 | Dutcher | 128/785 |
| 4,475,560 | 10/1984 | Tarjan et al. | 128/785 |
| 4,577,643 | 3/1986 | Beranek | 128/785 |
| 4,590,949 | 5/1986 | Pohndorf | 128/785 |
| 4,624,266 | 11/1986 | Kane | 128/785 |
| 4,628,943 | 12/1986 | Miller | 128/785 |
| 4,649,938 | 3/1987 | McArthur | 128/785 |
| 4,667,686 | 5/1987 | Peers-Travarton | 128/419 P |
| 4,842,590 | 6/1989 | Tanabe et al. | 128/656 |

Primary Examiner—Lee S. Cohen
Assistant Examiner—Kennedy J. Schaetzle
Attorney, Agent, or Firm—John R. Merkling

[57] ABSTRACT

An implantable endocardial lead with retractable fixation apparatus. The fixation apparatus comprises a sharpened helix which can be repeatedly both retracted within an electrode at a distal end of the lead and displaced outside the electrode by action of a flexible, tubular lanyard. The lanyard passes through a lumen from a proximal end of the lead to the distal end of the lead, where the lanyard is attached to a piston supporting the helix. At the proximal end of the lead, a jig moves the lanyard with respect to a longitudinal axis of the lead. When the helix is in an exposed position, torque can be transmitted from the proximal end of the lead to the distal end thereof, through the electrode to the piston and then to the helix to screw the helix into the endocardial tissue. To stiffen the lead during implantation, a stylet can be inserted into a lumen in the lanyard.

10 Claims, 2 Drawing Sheets

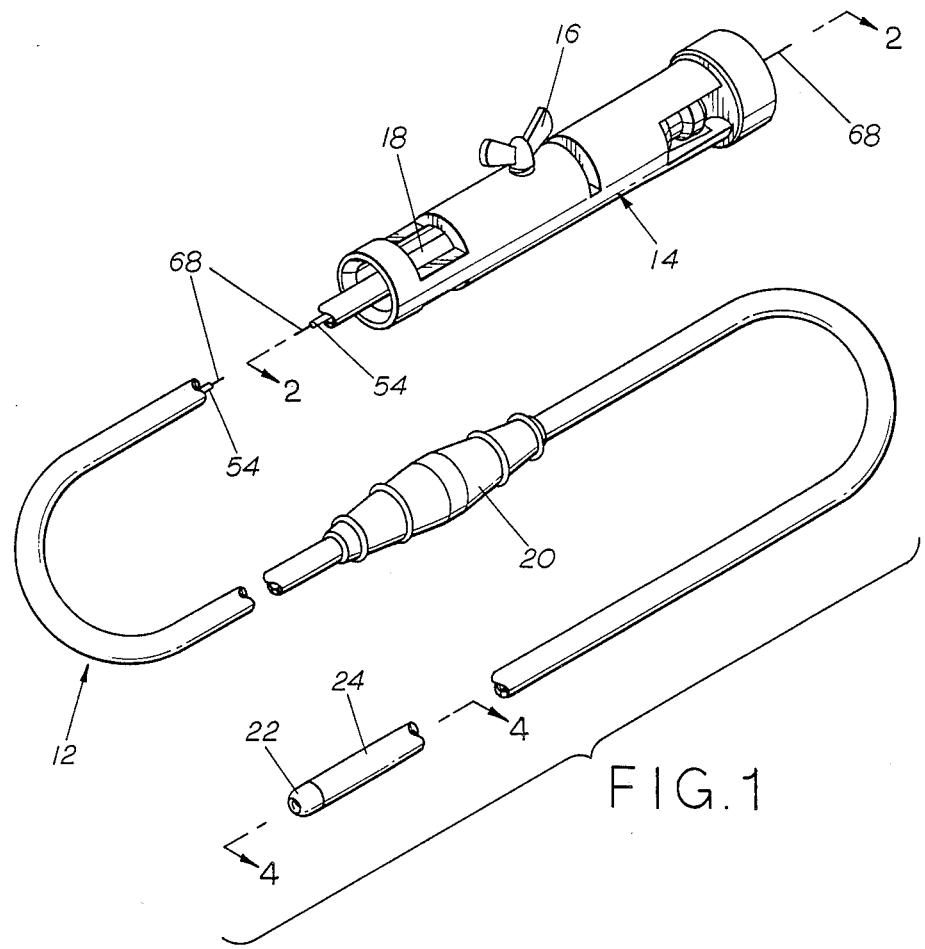
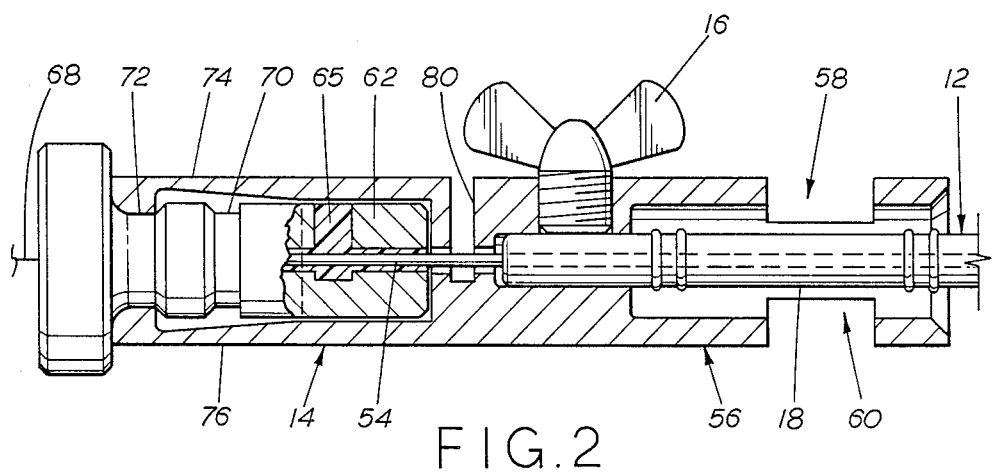

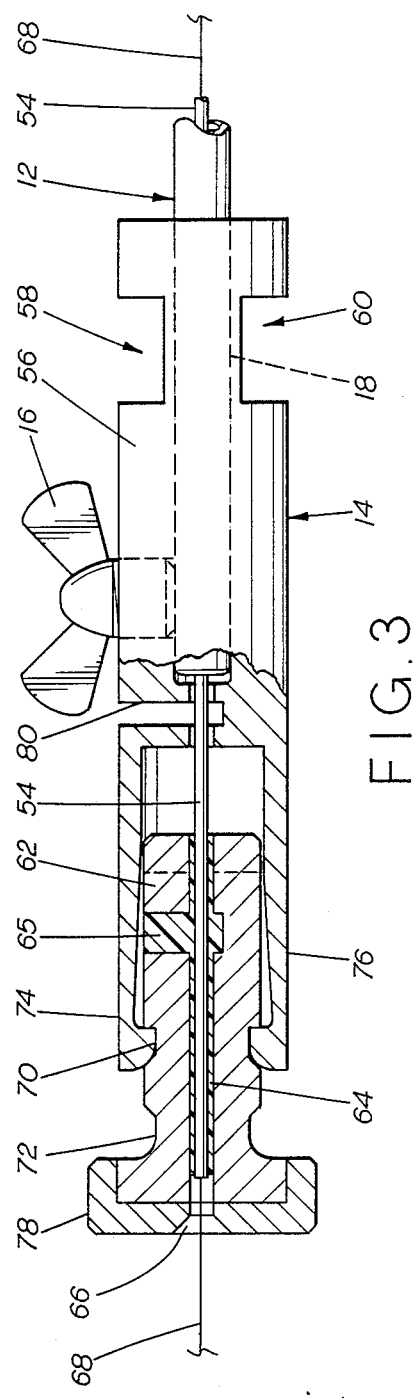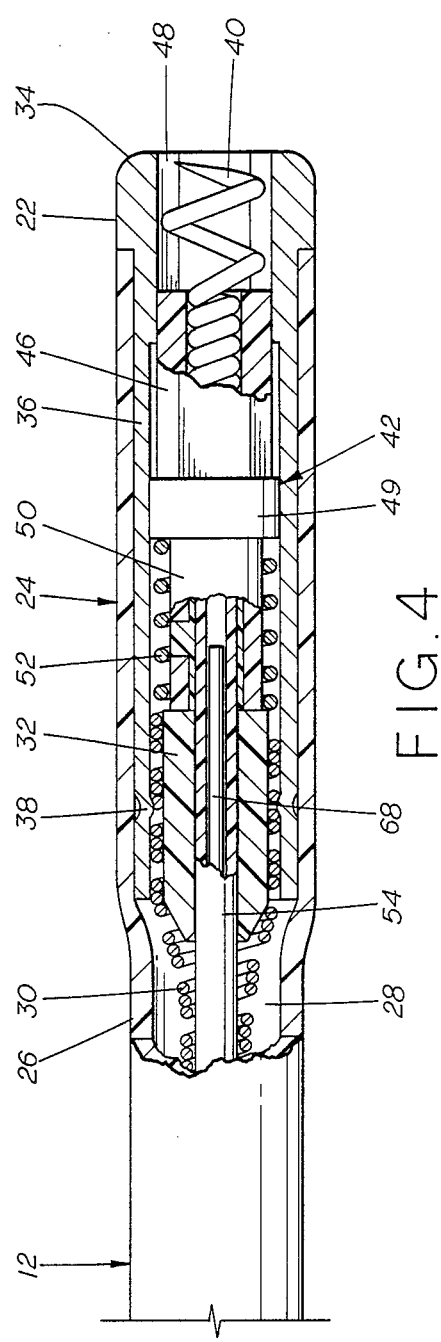

IMPLANTABLE ENDOCARDIAL LEAD WITH FIXATION APPARATUS RETRACTALBE BY A LANYARD

BACKGROUND OF THE INVENTION

1. Field of the Invention

The present invention relates generally to cardiac stimulation, and more particularly to an implantable endocardial lead which stimulates or senses electrical activity of the heart and which employs a retractable fixation mechanism which can be repeatedly exposed to or shielded from tissue during the process of securing the lead to cardiac tissue.

2. Prior Art

There are generally two types of body implantable leads used with cardiac pacemakers—one which requires surgery to expose the myocardial tissue to which an electrode is affixed and another which can be inserted through a body vessel, such as a vein, into the heart where an electrode contacts the endocardial tissue. In the latter type, the endocardial lead is often secured to the heart through the endothelial lining by a sharpened helix affixed to a distal end of the lead. When the end of the lead contacts the lining of the heart at a desired location, the lead may be secured in place by rotating the lead, thus screwing the helix into the heart tissue.

Such a system has been relatively effective in securing an endocardial lead once the initial location of the lead has been achieved. However, it is known that it is undesirable to expose the sharpened helix while the lead is being inserted through a blood vessel into the heart. Moreover, it is difficult to precisely place an endocardial lead on the first attempt. It is common, therefore, for a physician to repeatedly attempt to attach an endocardial lead having a sharpened helix securing means. It is desireable, therefore, to be able to shield the sharpened helix during the insertion of the lead through the vein and between attempts to implant the lead on the heart lining.

In the prior art, various apparatus have been proposed for achieving the desired result. For example, U.S. Pat. No. 3,974,834 to Lawrence M. Kane, discloses an implantable intervascular lead having an accordion-fold sleeve surrounding a helix. The sleeve is retractable to expose the helix and re-expandable to cover the helix in the event the helix is unscrewed and withdrawn. An object of the invention is to permit the lead to be inserted into and guided through a body vessel without snagging the body vessel.

Another attempt at solving these problems is disclosed in U.S. Pat. No. 4,146,036 to Robert G. Dutcher and Albert S. Benjamin. This patent discloses a body implantable, intervascular lead, having a helix fixation means. Apparatus for shielding the helix comprises a moveable piston or shaft located within the coils of the helix. The shaft is springloaded in a retracted position by the action of an elastomeric boot which also serves to seal off body fluids from the interior of the lead. A stylet passes through a lumen in the lead and acts against a proximal end of the shaft to force the shaft forward through the helix thus forming a partial barrier and inhibiting the helix from coming in contact with tissue, at least in the axial direction.

In U.S Pat. No. 4,649,938 to William A. McArthur, an endocardial lead with an extendible/retractable helix fixation means is described. The helix is mounted on a bobbin carried within the electrode tip. The bobbin and helix are retracted into the electrode tip by the action of a spring and are extended out of the tip by pressure from the end of the stylet inserted through a lumen in the lead.

SUMMARY OF THE INVENTION

The present invention provides an implantable endocardial lead with retractable fixation means. In the preferred embodiment, the fixation means comprises a sharpened helix which can be repeatedly both retracted within an electrode at a distal end of the lead and displaced outside the electrode. The lead defines an lumen from its proximal to its distal end. A lanyard passes through the lumen from the proximal end of the lead to the distal end of the lead, where the lanyard is attached to a piston supporting the helix. At the proximal end of the lead, means are provided for moving the lanyard with respect to a longitudinal axis of the lead. When the helix is in an exposed position, torque can be transmitted from the proximal end of the lead to the distal end thereof, through the electrode to the piston and thence to the helix to screw the helix into the endocardial tissue. To stiffen the lead during implantation, a stylet can be inserted into a lumen in the lanyard.

It is a principal object of the present invention to provide an implantable endocardial lead with retractable fixation means wherein the fixation means can be repeatably shielded and exposed during the implantation process.

A further object of the invention is to provide a lead wherein the fixation means is selectively shielded within an electrode located at the distal end of the lead and wherein the fixation means is selectively exposed and shielded by the action of a lanyard.

Another object of the invention is to provide an implantable endocardial lead with retractable fixation means which can be repeatedly exposed and shielded by the action of an lanyard.

Another important object of the invention is to provide means for controlling the displacement of the lanyard during implantation of the lead.

These and other objects and features of the present invention will be apparent from the detailed description taken with reference to the accompanying drawings.

BRIEF DESCRIPTION OF THE DRAWINGS

FIG. 1 is a prospective view of an implantable endocardial lead and a jig for controlling the displacement of a lanyard according to the present invention;

FIG. 2 is a sectional view of the jig for controlling the displacement of the lanyard taken along line 2—2 of FIG. 1;

FIG. 3 is an additional cross sectional view of the jig of FIG. 2, showing a cross section of a plunger; and FIG. 4 is a cross section of a distal end of the lead of FIG. 1 taken along lines 4—4.

DETAILED DESCRIPTION OF THE PREFERRED EMBODIMENT

Reference is now made to the drawings, wherein like numerals designate like parts throughout. FIG. 1 shows an assembly, generally designated 10, comprising an endocardial lead 12 and a jig 14. A wing-nut 16 secures a proximal end 18 of the lead 12 in the jig 14. The lead 12 has a suture sleeve 20 which slides along the lead 12 and which can be attached at an entrance into a vein of a patient in a conventional manner. The lead 12 also has an electrode 22 located at a distal end 24 of the lead.

As shown in FIG. 4, the lead 12 comprises a silicon or polyurethane sheath 26 which defines a lumen 28 along a longitudinal axis of the lead 12. Within the lumen 28, there is a coil conductor 30 for transmitting electrical impulses between the electrode 22 and the proximal end 18 of the lead 12. In the illustrated embodiment, a trifilar conductor is shown as the coil conductor 30. The coil conductor 30 wraps around a crimp slug 32 at the distal end 24 of the lead 12.

The electrode 22 comprises a ring contact 34 and a conductive sleeve 36. The conductive sleeve 36 fits over the crimp slug 32 and the coil conductor 30 and the three elements just mentioned are secured together by a crimp 38 in the conductive sleeve 36. The silicon sheath 26 encloses the conductive sleeve 36 of the electrode 22 to the ring contact 34.

In the illustrated embodiment, a fixation means is illustrated by a sharpened helix 40. A piston 42 supports the helix 40 in relatively constant alignment along the longitudinal axis of the lead 12. The piston 42 comprises a sealing ring 49 which slidably engages the conductive sleeve 36. On the distal side of the sealing ring 49, the piston 42 forms an hexagonal male member 46 which slidably engages an hexagonal female member 48 in the electrode 22. The hexagonal shape of the two members 46, 48 permits torque to be transmitted from the proximal end 18 of the lead 12 to the distal end 24 of the lead 12 and through the piston 42 to the helix 40 to screw the helix 40 into the endocardial tissue of the patient.

The piston 42 also comprises a stabilizing shaft 50 on the proximal side of the sealing ring 49. The stabilizing shaft 50 is slightly smaller in diameter than the crimp slug 32 so that a spring 52 can be interposed between the crimp slug 32 and the sealing ring 49 to assist in displacing the helix 40 outside of the electrode 22.

A lanyard 54 passes through the lumen 28 in the lead 12 from the proximal end 18 to the distal end 24 thereof. In the preferred embodiment, the lumen 54 is composed of a material such as polyamide which is relatively incompressible and inextensable but flexible so that pushing and pulling forces can be transmitted from the proximal end 18 of the lead 12 to the piston 42 through the bendable lead 12. The lanyard 54 is hollow so that a stylet 69 can be inserted through the lanyard 54 to stiffen the lead 12 during insertion in the body of the patient. The lanyard 54 passes slidably through the center of the crimp slug 32 and is adhesively secured to the stabilizing shaft 50.

At the proximal end 18 of the lead 12, the lanyard 54 is secured to the jig 14, as shown in FIG. 2. The jig 14 comprises a jig body 56. The wing-nut 16 clamps the proximal end 18 of the lead 12 into the jig body 56. Apertures 58 and 60 are provided so that electrical contact with the lead 12 can be made while the jig 14 is secured to the lead 12. During implantation, electrical signals will be sent through and received from the electrode 22 to verify the accurate positioning of the electrode 22.

The lanyard 54 passes through the body 56 of the jig 14 and into a plunger 62. As seen in FIG. 3, the lanyard 54 is adhesively secured at a distal end of a bore 64 in the plunger 62. To provide adhesion, epoxy filler may be injected into an aperture 65 in the plunger 62. At a proximal end of the bore 64, the bore 64 is countersunk to form an insertion funnel 66. The insertion funnel 66 aides a physician in inserting the stylet 62 into the bore 64 and through the lanyard 54 to the distal end of the lead 12. To facilitate movement of the plunger 62, the proximal end of the plunger is provided with a knob 78. The plunger 62 also has first and second circumferential notches 70, 72. Opposing clips 74, 76 selectively engage the notches 70, 72 to hold the plunger 62 in one of two selectable positions. In the first position, shown in FIG. 3, the clips 74, 76 engage the first circumferential notch 70 so that the lanyard 54 is placed in tension and the helix 40 is withdrawn within the electrode 22. In the second position, shown in FIG. 2, the clips 74, 76 engage the second circumferential notch 72 so that the lanyard 54 is placed in compression and the sharpened helix 40 is exposed outside of the electrode 22.

During implantation, the sharpened helix 40 can be repeatedly moved into and out of the electrode 22 until proper placement has been achieved. Then the physician can withdraw the stylet 68 and sever the lanyard 54 with a scalpel placed in a scalpel slot 80 in the body 56 of the jig 14. The wingscrew 16 can then be loosened and the jig 14 removed from the proximal end 18 of the lead 12. The proximal end of the lead 12 can then be inserted into an appropriate medical device, such as an implantable cardiac pacemaker.

The invention may be embodied in other specific forms without departing from the spirit or essential characteristics thereof. The present embodiment is therefore considered in all aspects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by U.S. Letters Paten is:

1. A lead assembly for implantation in a patient, the assembly comprising:
   an electrode adapted for insertion into a chamber of the patient's heart for electrical stimulation thereof and having a lumen extending through the electrode from a proximal end to a distal end thereof;
   a lead connected to said proximal end of the electrode at a distal end of the lead and adapted to transmit electrical impulses between the electrode and a proximal end of the lead, the lead having a lumen extending through the lead from the proximal end to the distal and thereof,
   fixation means for securing the electrode to the lining of the heart chamber, the fixation means being in slidable contact with the electrode in the lumen thereof,
   means for preventing relative angular movement of the fixation means with respect to the electrode, and
   a lanyard attached to a proximal end of the fixation means for displacing the fixation means along a longitudinal axis of the electrode to selectively expose at least part of the fixation means outside the electrode or withdraw the fixation means within the electrode, the lanyard being slidably disposed within the lumen of the lead and comprising a lumen for slidably and removably receiving a stylet.

2. An assembly according to claim 1 wherein the lanyard comprises a polyamide tube.

3. an assembly according to claim 2 wherein the fixation means comprise a sharpened helix.

4. A lead assembly for implantation in a patient, the assembly comprising:

an electrode adapted for insertion into a chamber of the patient's heart for electrical stimulation thereof and having a lumen extending through the electrode from a proximal end to a distal end thereof;

a lead connected to said proximal end of the electrode at a distal end of the lead and adapted to transmit electrical impulses between the electrode and a proximal end of the lead, the lead having a lumen extending through the lead from the proximal end to the distal and thereof, fixation means for securing the electrode to the lining of the heart chamber, the fixation means being in slidable contact with the electrode in the lumen thereof, means for preventing relative angular movement of the fixation means with respect to the electrode, a lanyard attached to a proximal end of the fixation means for displacing the fixation means along a longitudinal axis of the electrode to selectively expose at least part of the fixation means outside the electrode or withdraw the fixation means within the electrode, and means for selectively securing the lanyard in at least one pre-determined position.

5. An assembly according to claim 4 wherein the securing means comprise means for alternatively securing the lanyard in one of two pre-determined positions.

6. An assembly according to claim 5 wherein the means for alternatively securing the lanyard comprises a plunger and wherein the lanyard is attached at a proximal end thereof to a distal end of the plunger.

7. An assembly according to claim 6 wherein the lanyard is slidably disposed within the flexible lumen of the lead.

8. An assembly according to claim 7 wherein the lanyard comprises a lumen for slidably and removably receiving a stylet.

9. An assembly according to claim 8 wherein the lanyard comprises a polyamide tube.

10. An assembly according to claim 9 wherein the fixation means comprise a sharpened helix.

* * * * *